United States Patent
Choi et al.

(10) Patent No.: US 10,152,570 B2
(45) Date of Patent: Dec. 11, 2018

(54) METHOD AND APPARATUS FOR PROCESSING MEDICAL IMAGE DATA

(71) Applicant: Samsung Electronics Co., Ltd, Gyeonggi-do (KR)

(72) Inventors: Ji-woong Choi, Suwon-si (KR); Se-jae Goh, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 97 days.

(21) Appl. No.: 15/341,768

(22) Filed: Nov. 2, 2016

(65) Prior Publication Data

US 2017/0140098 A1     May 18, 2017

(30) Foreign Application Priority Data

Nov. 18, 2015    (KR) .......................... 10-2015-0161722

(51) Int. Cl.
*G06K 9/00*     (2006.01)
*G06F 19/00*    (2018.01)
(Continued)

(52) U.S. Cl.
CPC .......... *G06F 19/321* (2013.01); *G06T 1/0007* (2013.01)

(58) Field of Classification Search
USPC ....... 382/100, 103, 128, 134, 154–155, 162, 382/168, 173, 181, 190, 206, 219, 224,
(Continued)

(56) References Cited

U.S. PATENT DOCUMENTS

| 7,697,741 B2 | 4/2010 | Wang et al. |
| 2001/0019587 A1 | 9/2001 | Hashimoto et al. |

(Continued)

FOREIGN PATENT DOCUMENTS

| EP | 2 706 476 A2 | 3/2012 |
| JP | 2001251596 A | 9/2001 |

(Continued)

OTHER PUBLICATIONS

Korean Notice of Allowance for Korean Application No. 10-2015-0161722, dated Sep. 29, 2017. (4 pages).

*Primary Examiner* — Seyed Azarian

(57) ABSTRACT

An apparatus for processing medical image data, includes a controller configured to select an image group including pieces of original image data according to a digital imaging and communication in medicine (DICOM) standard. The controller is also configured to generate hierarchy information regarding a hierarchy structure of the image group by analyzing each piece of the original image data included in the image group, generate common data information by extracting, from each piece of the original image data, common data elements regarding respective classes that form the hierarchy structure based on the hierarchy information, generate common information regarding the image group based on the hierarchy information and the common data information, and perform data processing on the image group based on the common information. The apparatus also includes a memory configured to store the common information including the hierarchy information and the common data information.

17 Claims, 13 Drawing Sheets

(51) Int. Cl.
  *G06T 1/00* (2006.01)
  *G06Q 10/00* (2012.01)
(58) Field of Classification Search
  USPC ....... 382/220, 232, 254, 274, 276, 294, 305,
          382/312; 709/219; 707/769; 705/2
  See application file for complete search history.

(56) References Cited

U.S. PATENT DOCUMENTS

| | | | |
|---|---|---|---|
| 2008/0027908 A1* | 1/2008 | Durbeck | G06F 17/30516 |
| 2010/0135554 A1* | 6/2010 | Kohlmann | G06T 15/08 |
| | | | 382/128 |
| 2011/0131234 A1* | 6/2011 | Sasai | G06Q 10/00 |
| | | | 707/769 |
| 2013/0096941 A1* | 4/2013 | Kanada | G06F 19/3443 |
| | | | 705/2 |
| 2014/0074985 A1* | 3/2014 | Wallace | G06F 19/321 |
| | | | 709/219 |
| 2015/0085940 A1 | 3/2015 | Rhyu et al. | |

FOREIGN PATENT DOCUMENTS

| | | |
|---|---|---|
| JP | 2008-142150 A | 6/2008 |
| JP | 2010128787 A | 6/2010 |
| KR | 2001-0002074 A | 1/2001 |
| KR | 2003-0012727 A | 2/2003 |
| KR | 2006-0076686 | 7/2006 |
| KR | 100878291 B1 | 1/2009 |
| KR | 2013-0119316 A | 10/2013 |
| KR | 1020130120147 A | 11/2013 |
| KR | 1020150063243 A | 6/2015 |
| WO | WO 2015-046641 A1 | 4/2015 |

* cited by examiner

FIG. 3

| ☐ IM01 | ☐ IM02 | ☐ IM03 |
|---|---|---|
| ☐ IM04 | ☐ IM05 | ☐ IM06 |
| ☐ IM07 | ☐ IM08 | ☐ IM09 |
| ☐ IM10 | ☐ IM11 | ☐ IM12 |
| ☐ IM13 | ☐ IM14 | ☐ IM15 |
| ☐ IM16 | ☐ IM17 | ☐ IM18 |
| ☐ IM19 | ☐ IM20 | ☐ IM21 |
| ☐ IM22 | ☐ IM23 | ☐ IM24 |
| ☐ IM25 | ☐ IM26 | ☐ IM27 |
| ☐ IM28 | ☐ IM29 | ☐ IM30 |
| ☐ IM31 | ☐ IM32 | ☐ IM33 |
| ☐ IM34 | ☐ IM35 | ☐ IM36 |
| ☐ IM37 | ☐ IM38 | ☐ IM39 |
| ☐ IM40 | ☐ IM41 | ☐ IM23 |
| ☐ IM43 | ☐ IM44 | ☐ IM45 |
| ☐ IM46 | ☐ IM47 | ☐ IM48 |
| ☐ IM49 | ☐ IM50 | ☐ IM51 |
| ☐ IM52 | ☐ IM53 | ☐ IM54 |
| ☐ IM55 | ☐ IM56 | ☐ IM57 |
| ☐ IM58 | ☐ IM59 | ☐ IM60 |
| ☐ IM61 | ☐ IM62 | ☐ IM63 |
| ☐ IM64 | ☐ IM65 | ☐ IM66 |
| ☐ IM67 | ☐ IM68 | ☐ IM69 |
| ☐ IM70 | ☐ IM71 | ☐ IM72 |
| ☐ IM73 | ☐ IM74 | ☐ IM75 |
| ☐ IM76 | ☐ IM77 | ☐ IM78 |
| ☐ IM79 | ☐ IM80 | ☐ IM81 |
| ☐ IM82 | ☐ IM83 | ☐ IM84 |
| ☐ IM85 | ☐ IM86 | ☐ IM87 |
| ☐ IM88 | ☐ IM89 | ☐ IM90 |
| ☐ IM91 | ☐ IM92 | ☐ IM93 |
| ☐ IM94 | ☐ IM95 | |

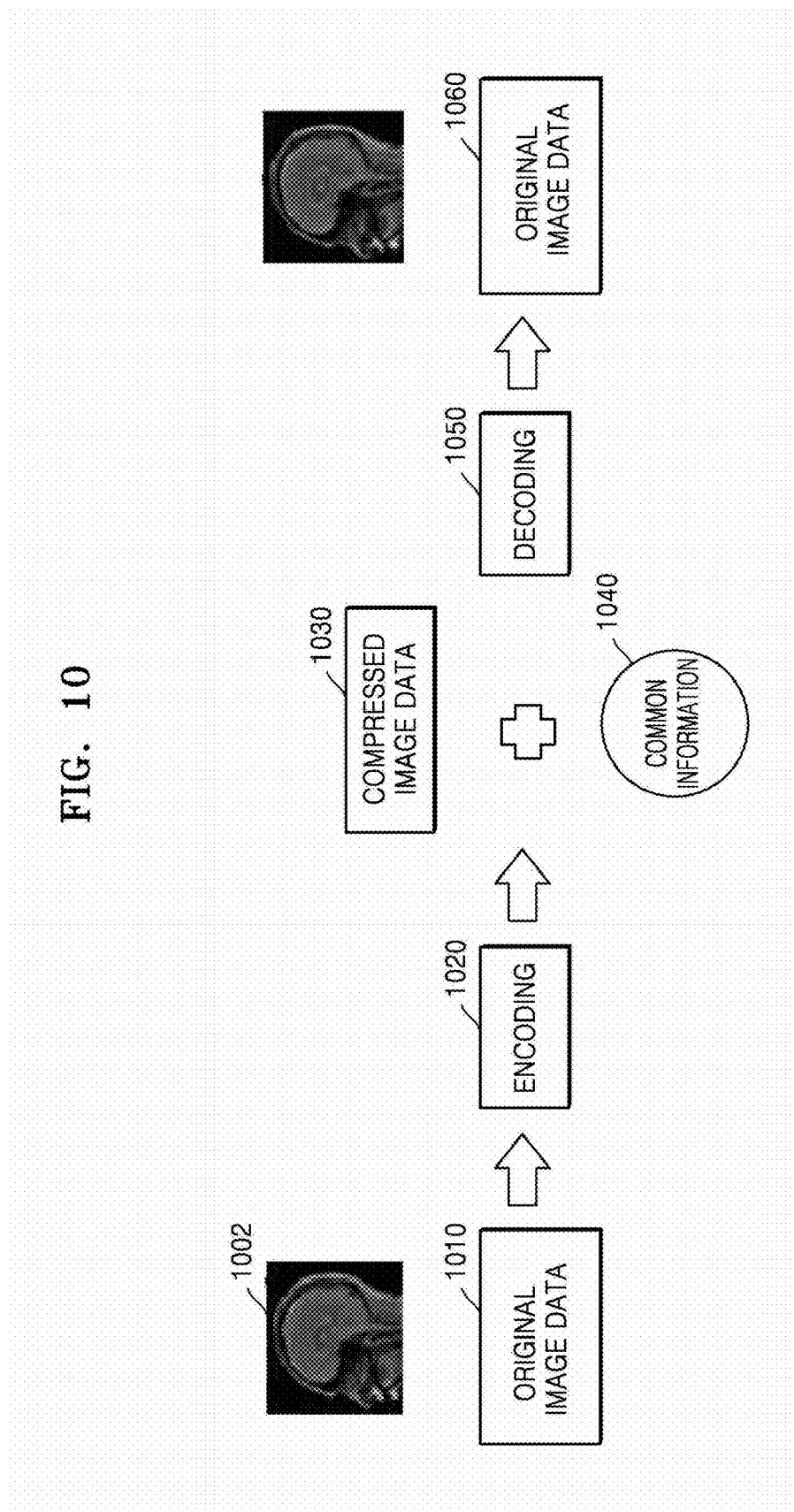

METHOD AND APPARATUS FOR PROCESSING MEDICAL IMAGE DATA

CROSS-REFERENCE TO RELATED APPLICATION(S) AND CLAIM OF PRIORITY

The present application is related to and claims the benefit under 35 U.S.C. § 119(a) of a Korean Patent Application No. 10-2015-0161722, filed on Nov. 18, 2015, in the Korean Intellectual Property Office, the disclosure of which is incorporated herein in its entirety by reference.

TECHNICAL FIELD

The present application relates generally to methods and apparatuses for processing medical image data and, more specifically, to methods and apparatuses for improving data processing efficiency of medical image data.

BACKGROUND

Digital imaging and communication in medicine (DICOM) is a standard for storing and transmitting medical images and information about the medical images and for exchanging image data between different medical image devices.

The DICOM standard uses an information model that has a hierarchy structure including classes such as patient, study, series, and image (instance). Due to the hierarchy structure, data included in a certain lower class has common information regarding a certain upper class. That is, the study, series, and image (instance) classes included in one patient class have common information regarding the patient class, and the series and image (instance) classes included in one study class have common information regarding the study class. Likewise, images (instances) included in one series class have common information regarding the series class.

The common information may be unnecessary duplicate information in image data processing procedures. For example, when pieces of image data according to the DICOM standard are compressed, respective pieces of the image data are recognized as being independent in a general compression process so that the duplicate information is repeatedly compressed. Thus, compression efficiency may decrease. Also, the duplicate information is repeatedly transmitted in an image data transmission operation. Thus transmission speed may decrease.

Therefore, it is necessary to increase efficiency of processing image data according to the DICOM standard.

SUMMARY

To address the above-discussed deficiencies, it is a primary object to provide, methods and apparatuses for processing image data which may improve data processing efficiency during an operation of processing image data according to a Digital imaging and communication in medicine (DICOM) standard.

In particular, provided are methods and apparatuses for processing image data which may improve data processing efficiency by generating common data information regarding common data elements and hierarchy information regarding a hierarchy structure based on image groups including pieces of image data according to the DICOM standard and processing data regarding the image groups based on the generated hierarchy information and common data information.

Additional aspects will be set forth in part in the description which follows and, in part, will be apparent from the description, or may be learned by practice of the presented embodiments.

According to an aspect of an embodiment, an apparatus for processing medical image data, includes: a controller configured to select an image group including pieces of original image data according to a digital imaging and communication in medicine (DICOM) standard, generate hierarchy information regarding a hierarchy structure of the image group by analyzing each piece of the original image data included in the image group, generate common data information by extracting, from each piece of the original image data, common data elements regarding respective classes that form the hierarchy structure based on the hierarchy information, generate common information regarding the image group based on the hierarchy information and the common data information, and perform data processing on the image group based on the common information; and a memory configured to store the common information including the hierarchy information and the common data information.

When generating the common data information, the controller be further configured to: extract common data elements regarding a first class; extract common data elements regarding a second class from among the extracted common data elements regarding the first class, wherein the second class is higher than the first class; and delete the common data elements regarding the second class from the common data elements regarding the first class.

The first class may be a lowermost class.

When the data processing is performed on the image group based on the common information, the controller may be further configured to generate compressed image data by deleting the common data elements from each piece of the original image data included in the image group based on the common information.

The apparatus of claim may further include a transceiver configured to receive/transmit data. When the data processing is performed on the image group based on the common information, the controller may be further configured to control the transceiver to transmit the common information to an external device and transmit, to the external device, remaining data that remains after the common data elements are excluded from the pieces of the original image data included in the image group based on the common information.

When the image group including the pieces of the original image data is selected, after pieces of image data are generated, the controller may be further configured to select the generated pieces of the image data as the image group according to a set unit.

The set unit may include a time unit or a patient unit.

The common data information may include common meta information and common image binary information of each piece of the original image data.

According to an aspect of another embodiment, an apparatus for processing medical image data, includes: a controller configured to load common information including hierarchy information and common data information that are generated based on an image group including pieces of original image data according to a digital imaging and communication in medicine (DICOM) standard, analyze a hierarchy structure of the image group based on the hierarchy information included in the common information, analyze common data elements regarding respective classes forming the hierarchy structure based on the common data information included in the common information, and restore at least one of the pieces of the original image data based on a result of both analyses; and a memory configured to store the common information including the hierarchy information and the common data information.

When the at least one of the pieces of the original image data is restored based on the result of both analyses, the controller may be further configured to restore the at least one of the pieces of the original image data by adding deleted common data elements to compressed image data from which the common data elements are deleted based on the common data information.

When the at least one of the pieces of the original it rage data is restored based on the result of both analyses, the controller may be further configured to extract common data elements regarding a third class, add the extracted common data elements regarding the third class to the compressed image data, extract common data elements regarding a fourth class that is lower than the third class, and add the extracted common data elements regarding the fourth class to the compressed image data.

The third class may be an uppermost class.

The apparatus may further include a transceiver configured to receive/transmit data. The controller may be further configured to control the transceiver to receive remaining data that remains after the common information and the common data elements are excluded from the pieces of the original image data included in the image group, and when the at least one of the pieces of the original image data is restored based on the result of both analyses, the controller may be further configured to restore the at least one of the pieces of the original image data by adding deleted common data elements to the remaining data based on the common data information.

When the at least one of the pieces of the original image data is restored based on the result of both analyses, the controller may be further configured to extract common data elements regarding a third class, add the extracted common data elements regarding the third class to the remaining data, extract common data elements regarding a fourth class that is lower than the third class, and add the extracted common data elements regarding the fourth class to the remaining data.

The third class may be an uppermost class.

The common data information may include common meta information and common image binary information of each piece of the original image data.

According to an aspect of another embodiment, a method of processing medical image data, includes: selecting an image group including pieces of original image data according to a Digital Imaging and Communication in Medicine (DICOM) standard; generating hierarchy information regarding a hierarchy structure of the image group by analyzing each piece of the original image data included in the image group; generating common data information by extracting common data elements regarding respective classes that form the hierarchy structure from each piece of the original image data, based on the hierarchy information; generating common information regarding the image group based on the hierarchy information and the common data information; and performing data processing on the image group based on the common information.

The generating of the common data information may include: extracting common data elements regarding a first class; extracting common data elements regarding a second class that is higher than the first class from among the common data elements extracted from the first class; and deleting the common data elements regarding the second class from the common data elements of the first class.

The first class may be a lowermost class.

The performing of the data processing may include generating compressed image data by deleting the common data elements from each piece of the original image data included in the image group based on the common information.

The performing of the data processing may include: transmitting the common information to an external device; and transmitting, to the external device, remaining data that remains after the common data elements are excluded from the pieces of the original image data included in the image group based on the common information.

The selecting of the image group including the pieces of the original image data may include, after pieces of image data are generated, selecting the generated pieces of the image data as the image group according to a set unit.

The set unit may include a time unit or a patient unit.

The common data information may include common meta information and common image binary information of each piece of the original image data.

According to an aspect of another embodiment, a method of processing medical image data, includes: loading common information including common data information and hierarchy information generated based on an image group including pieces of original image data according to a Digital imaging and Communication in Medicine (DICOM) standard; analyzing a hierarchy structure of the image group based on the hierarchy information included in the common information; analyzing common data elements regarding respective classes that form the hierarchy structure based on the common data information included in the common information; and restoring at least one of the pieces of the original image data based on a result of both analyses.

The restoring of the at least one of the pieces of the original image data may include restoring the at least one of the pieces of the original image data by adding deleted common data elements to compressed image data from which the common data elements are deleted based on the common data information.

The restoring of the at least one of the pieces of the original image data may include: adding common data elements regarding a third class to the compressed image data, wherein the common data elements regarding the third class are extracted; and adding, to the compressed image data, common data elements regarding a fourth class that is lower than the third class, wherein the common data elements regarding the fourth class are extracted.

The third class may be an uppermost class.

The method may further include: receiving the common information; and receiving remaining data that remains after the common data elements are excluded from the pieces of the original image data included in the image group, wherein the restoring of the at least one of the pieces of the original image data based on the result of both analyses may include restoring the at least one of the pieces of the original image data by adding deleted common data elements to the remaining data based on the common data information.

The restoring of the at least one of the pieces of the original image data based on the result of both analyses may include: adding common data elements regarding a third class to the remaining data, wherein the common data elements regarding the third class are extracted, and adding common data elements regarding a fourth class that is lower than the third class to the remaining data, wherein the common data elements regarding the fourth class are extracted.

The third class may be an uppermost class.

The common data information may include common meta information and common image binary information of each piece of the original image data.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 3 illustrates an image group according to an embodiment;

FIG. 10 illustrates an operation of compressing and restoring image data according to an embodiment;

DETAILED DESCRIPTION

Figure 1:
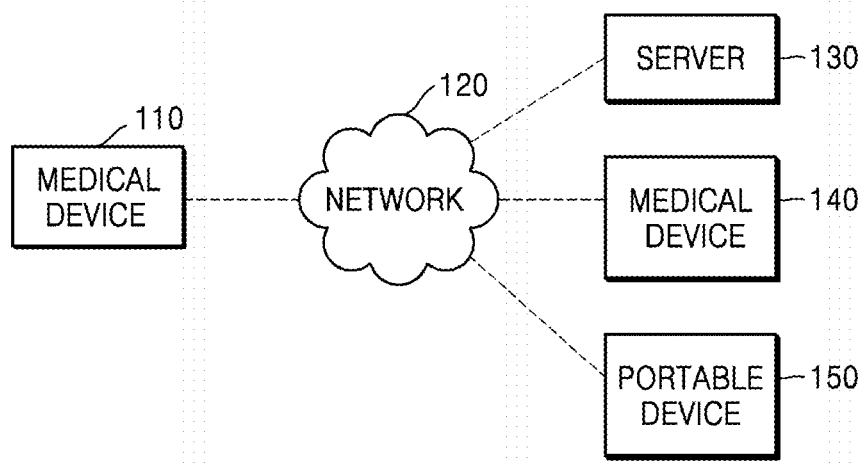
FIG. 1 illustrates a network environment in which medical image data is exchanged, according to an embodiment.

FIGS. 1 through 13, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged image processing system.

Terms used herein will be briefly explained, and then embodiments will be described in detail.

The terms used in this specification are those general terms currently widely used in the art in consideration of functions regarding the concepts described herein, but the terms may vary according to the intention of those of ordinary skill in the art, precedents, or new technology in the art. Also, specified terms may be selected by the applicant, and in this case, the detailed meaning thereof will be described in the detailed description of the concepts described herein. Thus, the terms used in the specification should be understood not as simple names but based on the meaning of the terms and the overall description of the concepts described herein.

Throughout the specification, when a portion "includes" an element, another element may be further included, rather than excluding the existence of the other element, unless otherwise described. Also, the term "unit" may be a software component or a hardware component such as a field programmable gate array (FPGA) or an application specific integrated circuit (ASIC) and may perform certain functions. However, the "unit" is not limited thereto. The "unit" may be included in a memory medium for performing addressing and may execute one or more processors. For example, the "unit" includes components such as software components, object-oriented software components, class components, and task components, segments such as processes, functions, properties, procedures, sub-routines, segments of program codes, drivers, firmware, micro codes, circuits, data, databases, data structures, tables, arrays, and variables. The components and the "units" may be combined into a smaller number of components and "units" or may be divided into additional components and "units".

With reference to the accompanying drawings, embodiments will be described so that one of ordinary skill in the art may easily implement the embodiments. The concepts described herein may, however, be embodied in many different forms and should not be construed as being limited to the embodiments set forth herein. For clarity, elements in the drawings that are not related to embodiments will be omitted.

In the specification, the term 'image data' may indicate multi-dimensional data including discrete image elements (e.g., pixels in a 2D image and voxels in a 3D image). For example, the image data may include medical image data obtained by a medical device such as a computed tomography (CT) imaging device, an X-ray imaging device, or a magnetic resonance imaging (MRI) image device.

Also, in the specification, the term 'original image data' indicates image data that is initially generated or obtained. That is, the original image data is initial image data for which data processing is not performed. However, the original image data is not limited thereto and may include image data restored after certain data processing is performed on the initial image data.

FIG. 1 illustrates a network environment in which medical image data is exchanged, according to an embodiment.

Referring to FIG. 1, the network environment in which the medical image data is exchanged may include medical devices 110 and 140, a network 120, a server 130, and a portable device 150. In the network environment, communication may be performed according to a Digital Imaging and Communication in Medicine (DICOM) standard. Also, image data exchanged in the network may be generated according to the DICOM standard. Furthermore, the network environment of FIG. 1 may be a picture archiving communication system (PACS).

The medical device 110 may include an apparatus (not shown) for processing medical image data. Also, the medical device 110 may perform at least one of the processes of generating, storing, and/or processing medical image data. In this case, the medical device 110 may generate the medical image data according to the DICOM standard or may store the medical image data generated according to the DICOM standard. Also, the apparatus for processing medical image data included in the medical device 110 may perform data processing on the generated or stored medical image data. In this case, the data processing may include a process of compressing data or a process of transmitting data to the server 130, the medical device 140, the portable device 150, and/or the like.

The medical device 110 may restore original image data based on the medical image data for which the data processing is performed by the medical device 110 or 140 using the apparatus for processing medical image data. Also, the original image data may be restored after the medical image data stored in the server 130, the medical device 140, the portable device 150, and/or the like is received. In this case, the restored original image data may be the medical image data that is generated according to the DICOM standard. Hereinafter, image data is medical image data that is obtained by a medical device such as computed tomography (CT) imaging device, an X-ray imaging device, or a magnetic resonance imaging (MRI) image device.

The network 120 connects the medical device 110 to the medical device 140, the portable device 150, and/or the like. In this case, the network 120 may include all networks, for example, Internet, Intranet, etc., which may be accessed by the medical device 110.

Figure 2A:
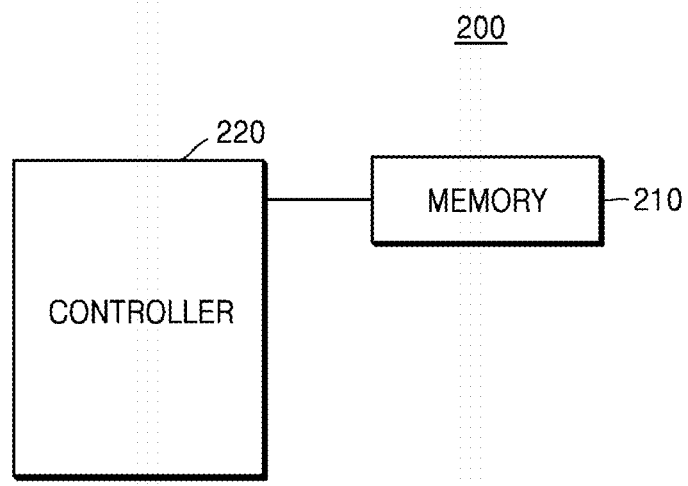
FIGS. 2A and 2B illustrate internal structures of apparatuses for processing medical image data, according to an embodiment.
Figure 2B:
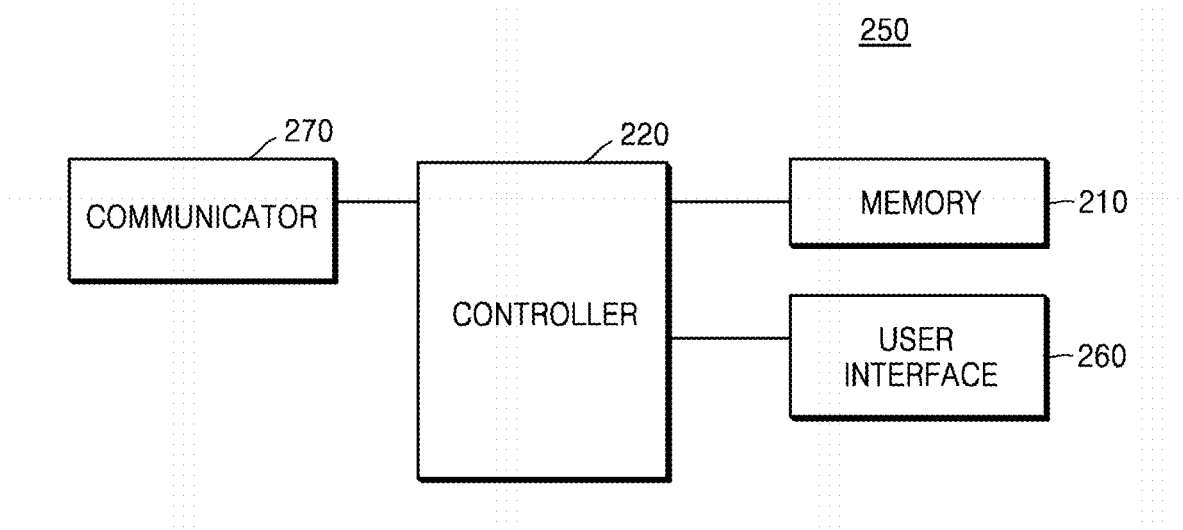

FIGS. 2A and 2B illustrate internal structures of apparatuses 200 and 250 for processing medical image data according to an embodiment.

Referring to FIG. 2A, the apparatus 200 for processing medical image data includes a memory 210 and a controller 220. The apparatus 200 for processing medical image data may be included in the medical devices 110 and 140, the server 130, the portable device 150, etc. which are described with reference to FIG. 1, and may perform data processing on the medical image data. In detail, the apparatus 200 for processing medical image data compresses the original image data or separate common data elements from remaining pieces of data among pieces of the medical image data in order to transmit the compressed original image data or the separated common data elements to another device. Also, the apparatus 200 for processing medical image data may restore the compressed medical image data as the original image data.

The memory 210 may include at least one type of storage media such as a flash memory type, a hard disk type, a multimedia card micro type, a card type memory (e.g., SD memory, XD memory, etc.), a Random Access Memory (RAM) type, a Static Random Access Memory (SRAM) type, a Read-Only Memory (ROM) type, an Electrically Erasable Programmable Read-Only Memory (EEPROM) type, a Programmable Read-Only Memory (PROM) magnetic memory type, a magnetic disc type, and an optical disc type. The memory 210 includes hierarchy information and common information including common data information. In detail, the memory 210 stores hierarchy information regarding a hierarchy structure of the image groups including the pieces of the original image data and common information including common data information that is information regarding common data elements regarding each class.

The controller 220 controls overall operations of the apparatus 200 for processing medical image data. In r core detail, the controller 220 may control an operation of processing medical image data overall.

The controller 220 selects the image groups including the pieces of the original image data according to the DICOM standard, generates the hierarchy information regarding the hierarchy structure of the image groups by analyzing each piece of the original image data included in the image groups, generates the common data information based on the hierarchy information by extracting common data elements regarding each class that forms the hierarchy structure from each piece of the original it age data, generates common information regarding the image groups based on the hierarchy information and the common data information, and performs data processing on the image groups based on the common information. Operations of the controller 220 will be described below with reference to FIGS. 3 to 10.

According to an embodiment, the controller 220 selects the image groups including the pieces of the original image data according to the DICOM standard.

FIG. 3 illustrates an image group according to an embodiment.

Referring to FIG. 3, ninety-five (95) pieces of original image data that are selected as one image group are in a file form. The controller 220 may select an image group according to a user input or may select an image group according to criteria. In a case where the image group is selected according to the user input, when a user selects pieces of the original image data that are in a file form, the controller 220 may select the selected pieces of the original image data as one image group.

According to an embodiment, the controller 220 performs data processing based on common information that pieces of image data commonly have, and thus, image data groups are used to extract the common information. The controller 220 selects the image data groups used to extract common information from the pieces of the original image data.

According to an embodiment, when the controller 220 selects the image group including the pieces of the original image data, the controller 220 may generate pieces of image data first and then may select the generated pieces of the image data as an image group according to a unit that is set. In this case, the set unit may be a time unit or a patient unit. For example, pieces of the original image data, which are generated at intervals of 5 or 10 minutes, may be selected as an image group. Also, pieces of the original image data which are generated by capturing an image of a certain patient may be selected as an image group. In this case, when the pieces of the original image data included in one image group are generated, the controller 220 may extract common information by comparing the generated pieces of the original image data with other pieces of the original image data included in the image group.

According to an embodiment, the controller 220 generates hierarchy information regarding a hierarchy structure of the image group by analyzing each piece of the original image data included in the image group.

Figure 4:
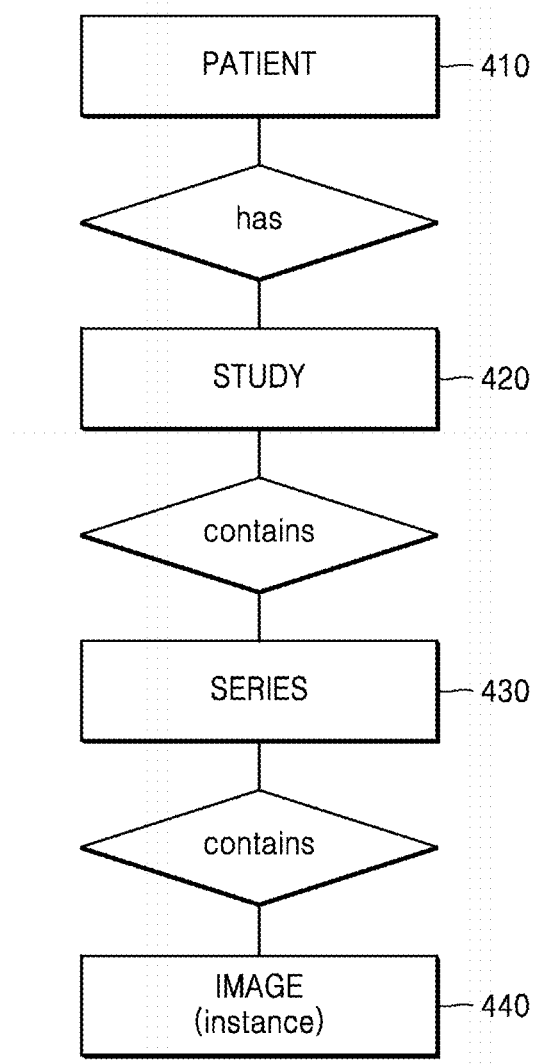
FIG. 4 illustrates an information model according to the digital imaging and communication in medicine (DICOM) standard.

FIG. 4 illustrates an information model according to the DICOM standard.

Referring to FIG. 4, as described above, the information model according to the DICOM standard has a hierarchy structure in which a patient 410, a study 420, a series 430, and an image (an instance) 440 are arranged in a stated order. An ascending order from the image (the instance) 440 to the patient 410 indicates that the patient 410 is an upper class, and a descending order from the patient 410 to the image (the instance) 440 indicates that the image (the instance) 440 is a lower class. The controller 220 determines which hierarchy structure each piece of the original image data included in the image group has by analyzing a structural relationship between the pieces of the original image data included in the image group. For example, among image groups shown in FIG. 3, pieces of original image data, that is, an IM01 to an IM23, are included in a patient class that is A. Among the IM01 to IM23, the pieces of the original image data, that is, the IM01 to IM08, are included in a study class that is B, and among the IM01 to IM08, the pieces of the original image data, that is, the IM01 to IM03, are included in a series class that is C. However, this is merely an example, and pieces of the original image data may be continuous or discontinuous. That is, discontinuous pieces of the original image data, that is, the IM09, the IM11, and the IM14, may be included in the study class that is B. Also, both continuous and discontinuous pieces of the original image data may be included in the study class that is B. As described above, the controller 220 analyzes a hierarchy structure of the image group by analyzing in which class each piece of the original image data is included and generates hierarchy information regarding the hierarchy structure.

According to an embodiment, the controller 220 extracts common data elements regarding each class that forms the hierarchy structure from each piece of the original image data based on the hierarchy information and generates common data information.

As the image group has the hierarchy structure according to the DICOM standard, data included in a class lower than a certain class has common information regarding the certain class that is higher in the hierarchy structure. That is, study, series, and image (instance) classes included in one patient class have common hierarchy information regarding the patient class, and series and image (instance) classes included in one study class have common hierarchy information regarding the study class. Likewise, image (instance) classes included in one series class have common hierarchy information regarding the series class.

When data processing is performed on each piece of the common information, data processing is repeatedly performed on the common information that is duplicate information. Therefore, image data processing efficiency decreases. In this case, when pieces of the common information are bound together in such a manner that the data processing is performed on the entire common information all at once, the image data processing efficiency may be improved.

The image data according to the DICOM standard includes data elements. In this case, each data element includes a tag in which a group number and an element number are combined with each other, value representation (VR) indicating a form of a data element, a length indicating a length of a data element, and a value indicating content of a data element. Accordingly, pieces of the original image data having the same hierarchy information have the same data elements regarding the hierarchy information. The controller 220 generates common data information by extracting the common data elements of each class. While generating the common data information, the controller 220 may extract common data elements by comparing the pieces of the original image data with each other.

Also, the common data elements may not always be included in the entire original image data, and the controller 220 may extract the common data elements from part of the original image data.

In this case, the common data information may include common meta information and common image binary information of each piece of the original image data. The common meta information is used to store values of tags that are duplicated, depending on the patient, study, and series classes. Also, the common image binary information is used to store values related to an image among pieces of the original image data. In this case, the values related to the image may be presented as the values of the tags such that the common image binary information may also be used to store values of duplicate tags. For example, the common image binary information may include values of duplicate pixel tags. The common meta information and the common image binary information will be described with reference to FIGS. 5 and 6.

Figure 5:
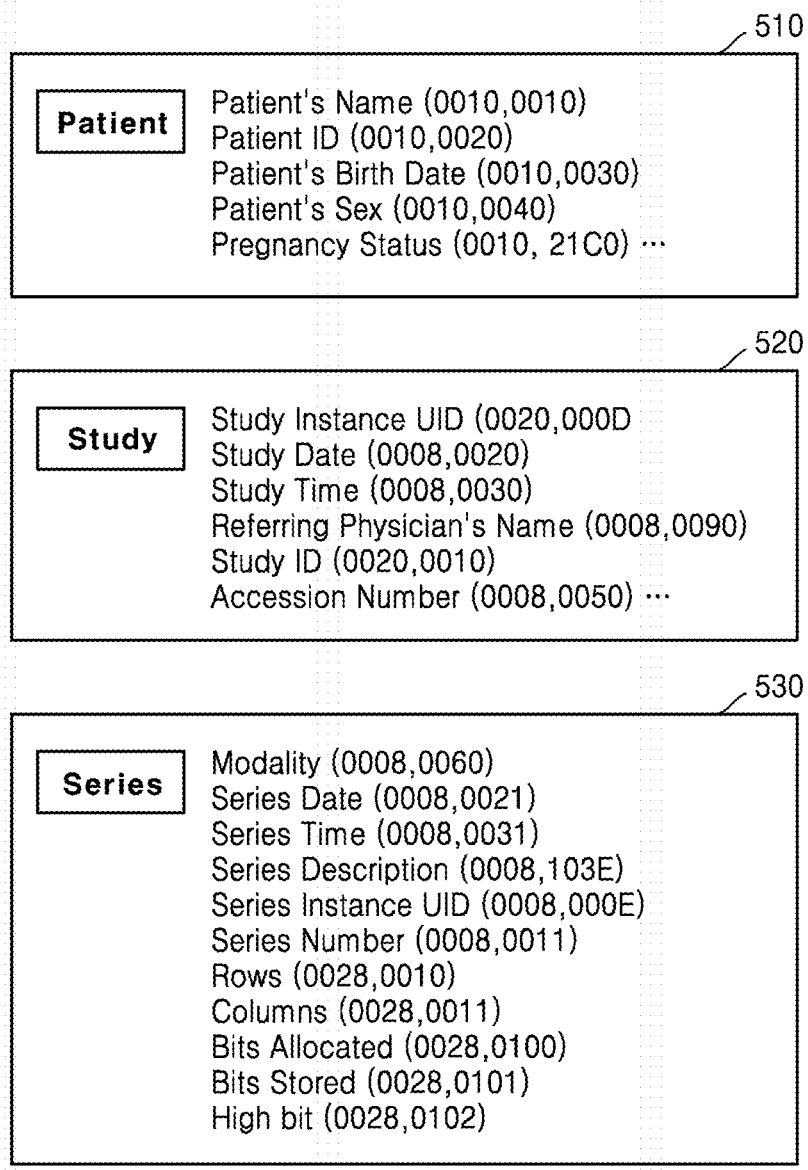
FIG. 5 illustrates common meta information according to an embodiment.

FIG. 5 illustrates common meta information according to an embodiment.

Referring to FIG. 5, each class includes different tags. A patient class 510 may include tags such as a patient's name, a patient ID, a patient's birthday, a patient's sex, a patient's status, etc. Also, a study class 520 may include tags such as a study instance UID, a study date, a study time, a referring physician's name, a study ID, an accession number, etc. Moreover, a series class 530 may include tags such as modality, a series date, a series time, a series description, a series instance UID, a series number, rows, columns, bits allocated, bits stored, a high bit, etc. The tags shown in FIG. 5 are merely examples of tags included in each class. Standard tags specified in standards and private tags defined by users may be included in the common meta information.

According to an embodiment, the controller 220 may extract, from each piece of the original image data, common data elements of each class that forms the hierarchy structure and may generate the common meta information.

In the case of the tags shown in FIG. 5, pieces of the original image data included in the study class 520 that is lower than the patient class 510 may include tags that are the patient's name, the patient ID, the patient's birthday, the patient's sex, and the patient's status, all of which have the same value. In this case, common data elements regarding the patient class 510 are the patient's name, the patient ID, the patient's birthday, the patient sex, and the patient status, and thus the controller 220 may generate common meta information including the patient's name, the patient ID, the patient's birthday, the patient's sex, and the patient's status. Furthermore, when pieces of the original image data which are included in the study class 520 and the series class 530 include tags having the same value, the tags may be used to generate common meta information.

Figure 6:
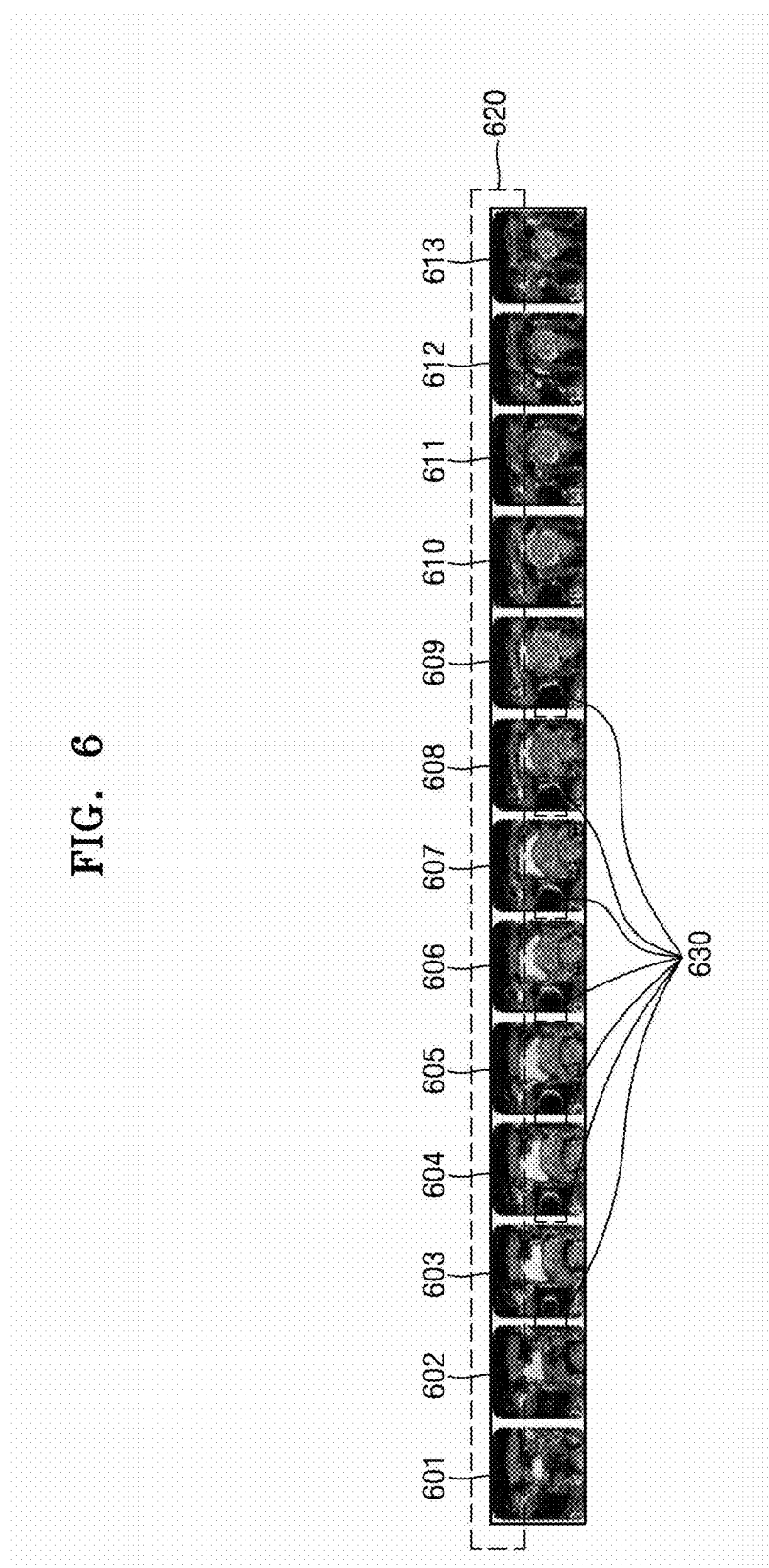
FIG. 6 illustrates common image binary information according to an embodiment.

FIG. 6 illustrates common image binary information according to an embodiment.

FIG. 6 shows 13 medical images 601 to 613. The medical images 601 to 613 have similar portions overall, and some of the medical images 601 to 613 have similar portions. Black regions 620 are commonly shown on upper portions of the medical images 601 to 613. Also, the medical images 603, 604, 605, 606, 607, 608 and 609 have similar portions 630 on left sides thereof. The black regions 620 and the similar portions 630 may each have sections that are exactly the same as one another. The sections that are exactly the same as one another may be common information of image data including the medical images 601 to 613. Common image binary information is used to store common values related to the medical images 601 to 613. For example, when the medical images 601 to 613 have pixels that are located at the same location and have the same color, the common image binary information may include tag values of the pixels.

According to an embodiment, when generating the common data information, the controller 220 may extract common data elements regarding a first class, extract common data elements regarding a second class, which is higher than the first class, from among the common data elements regarding the first class, and delete the common data elements regarding the second class from the common data elements regarding the first class. That is, the controller 220 extracts the common data elements regarding the first class first. Then, data elements, which are also found in the extracted common data elements regarding the second class, among the common data elements regarding the first class are stored as the common data elements regarding the second class. Furthermore, the common data elements regarding the second class are deleted from the common data elements regarding the first class such that identical data elements are not duplicated.

According to an embodiment, the first class may be a lowermost class. That is, the common data elements are extracted starting from the lowermost class to an upper class.

Figure 7:
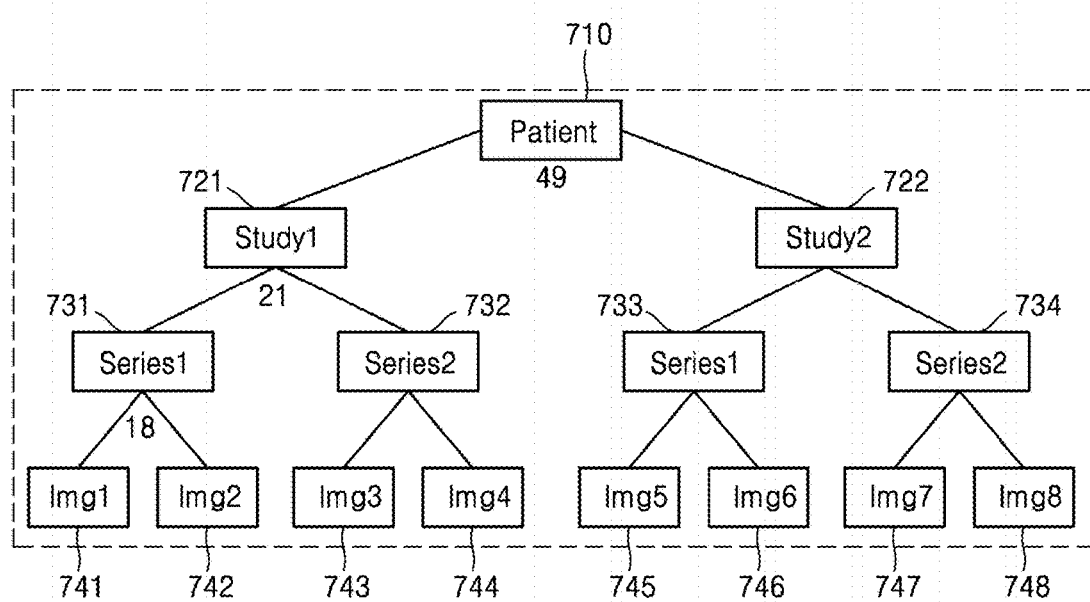
FIG. 7 illustrates extracted common data information according to an embodiment.

FIG. 7 illustrates extracted common data information according to an embodiment.

Referring to FIG. 7, a patient class 710 includes two study classes 721 and 722, and the study classes 721 and 722 each include two of series classes 731, 732, 733, and 734. Each of the series classes 731, 732, 733, and 734 includes two of images (instances) 741, 742, 743, 744, 745, 746, 747, and 748.

Based on the image 1 741, the image 1 741 is included in a series 1 731, the series 1 731 is included in the study 1 721, and the study 1 721 is included in the patient 710.

Referring to FIG. 7, when the image 1 741 has 88 pieces of common data information that the other images 742, 743, 744, 745, 746, 747, and 748 also have, the controller 220 may determine that the image 1 741 has 88 common data elements after comparing the image 1 741 with the images 742, 743, 744, 745, 746, 747, and 748. That is, when the series 1 731 includes 18 common data elements, the study 1 721 includes 21 common data elements, and the patient 710 includes 49 common data elements, the controller 220 may determine that the image 1 741 includes 88 common data elements after comparing the image 1 741 with the images 742, 743, 744, 745, 746, 747, and 748. However, the image 1 741 does not always have 88 common data elements that the other images 742, 743, 744, 745, 746, 747, and 748 also have.

The image 1 741 and the image 2 742 are included in the patient 710, the study 1 721, and the series 1 731 and thus may have common data elements of all classes. That is, the image 1 741 and the image 2 742 may include 18 common data elements regarding the series 1 731, 21 common data elements regarding the study 1 721, 49 common data elements regarding the patient 710 and thus may have 88 common data elements in total. According to an embodiment, the controller 220 may add the common data elements regarding the patient 710, the study 1 721, and the series 1 731 in order to extract and store the 88 common data elements as common data information regarding the series 1 731.

The image 1 741 and other images 742, 743, and 744 are included in the study 1 721. However, the image 1 741 and the image 2 742 are included in the series 1 731, but the image 3 743 and the image 4 744 are included in the series 2 732. Therefore, the images 742, 743, and 744 that are different from the image 1 741 may have the common data elements regarding the study class and the patient class. That is, the image 1 741 and the images 742, 743, and 744 may have 21 common data elements regarding the study 1 721 and 49 common data elements regarding the patient 710 and thus may have 70 common data elements in total. According to an embodiment, the controller 220 may extract the 70 common data elements as the common data information regarding the study 1 721 and may store the extracted common data elements. In this case, the controller 220 may delete, from the common data information regarding the series 1 731, the common data elements that the patient 710 and the study 1 721 commonly have. When the common data information is generated as described above, identical pieces of data may not be repeatedly stored.

Likewise, the image 1 741 and the other images 742, 743, 744, 745, 746, 747, and 748 only have 49 common data elements included in the patient 710 as the common data information. According to an embodiment, the controller 220 may extract the 49 common data elements as the common data information regarding the patient 710 and may store the extracted common data elements. In this case, the controller 220 may delete, from the common data information regarding the patient 710, the 49 common data elements regarding the patient 710.

The common data elements may be extracted starting from the lowermost class to an upper class, and thus the common data information may be generated without any duplicate information.

According to an embodiment, the controller 220 generates common information regarding the image group based on the hierarchy information 820 and the common data information 830. In more detail, the controller 220 may generate information regarding the hierarchy structure of the image group as hierarchy information 820 and generate common data elements regarding each class that forms the hierarchy structure. Then, the controller 220 combines the hierarchy information 820 and the common data information 830 with each other in order generate common information. The common information will be described with reference to FIG. 8.

Figure 8:
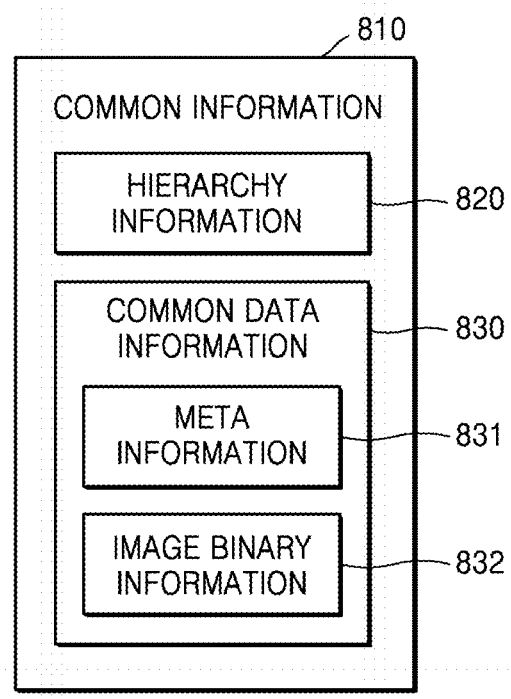
FIG. 8 illustrates common information according to an embodiment.

FIG. 8 illustrates common information 810 according to an embodiment.

Referring to FIG. 8, the common information 810 includes hierarchy information 820 and common data information 830. Also, the common data information 830 may include meta information 831 and image binary information 832. Therefore, the common information 810 may include information regarding which hierarchy structure an image group has and which common data elements are included in each class.

According to an embodiment, the controller 220 performs data processing on the image group based on the common information 810. The controller 220 performs data processing on the image group based on the common information 810. Thus, the data processing is not repeatedly performed on the common information 810 that is duplicate data, but may be performed on the common information 810 all at once. Therefore, image data processing efficiency may be improved.

According to an embodiment, when performing the data processing on the image group based on the common information 810, the controller 220 may generate compressed image data by deleting the common data elements from each piece of the original image data included in the image group based on the common information 810.

In a general compression process, pieces of image data are considered as independent pieces of data, and thus duplicate information is repeatedly compressed such that compression efficiency may decrease. In an embodiment compared with the general compression process, the common data elements are separately managed as common information, and the original image data is compressed by deleting the common data elements therefrom to thereby improve compression efficiency. That is, since duplicate pieces of data are not repeatedly compressed, and thus compression efficiency may be improved.

Referring to FIG. 2B, the apparatus 250 for processing medical image data may further include at least one of a user interface 260 and a communicator 270 in comparison with the apparatus 200 for processing medical image data shown in FIG. 2A. Components found in apparatuses 200 and 250 for processing medical image data are indicated by the same reference numerals, and descriptions thereof will not be repeated.

The user interface 260 receives a certain command or data from the user. In detail, the user interface 260 may include a touch screen, a mouse, a keyboard, an input device including hard keys for inputting certain data, or the like. For example, the user manipulates at least one of the touch screen, the mouse, the keyboard, or the input device included in the user interface 260 and may input certain data or a certain command thereto. According to an embodiment, the user interface 260 may receive, from the user, information used to select the pieces of the original image data included in one image group.

The communicator 270 may receive/transmit data according to control of the controller 220. The communicator 270 may communicate with an external device, an external medical device, or the like. For example, the communicator 270 may be connected to at least one of an external medical device, an external server, and an external portable device. The communicator 270 is connected to an external medical imaging device and thus may receive medical image data from the external medical imaging device or may receive/transmit data necessary to process, compress, and/or restore the medical image data from/to the external medical imaging device. According to an embodiment, when data processing is performed on the image group based on the common information, the communicator 270 may transmit the common information to the external device and may transmit remaining data, which remains after the common data elements are excluded from the pieces of the original image data included in the image group based on the common information, to the external device, according to the control of the controller 220.

According to an embodiment, when data processing is performed on the image group based on the common information, the controller 220 may control the communicator 270 to transmit the common information and the remaining data, which remains after the common data elements are excluded from the pieces of the original image data included in the image group based on the common information, to the external device. In this case, the controller 220 identifies the common data elements first based on the common information and may control the communicator 270 to transmit each piece of the original image data and the remaining data other than the common data elements.

In a general data transmission operation, since pieces of image data are respectively transmitted, transmission efficiency may decrease. In an embodiment compared with the general data transmission operation, common data elements are bound as common information for transmission, and remaining data other than the common data elements are respectively transmitted such that transmission efficiency may be improved. That is, duplicate data is transmitted only once, and thus, the transmission efficiency may be improved. Furthermore, according to an embodiment, other data processing is not performed on original data, and common data elements are separated from the original data during a transmission operation. Thus, the image data may be immediately used in a medical device according to a current DICOM standard.

An operation of processing data will be described below together with an operation of restoring an original image.

As described above, the apparatus 200 for processing medical image data according to an embodiment may perform data processing on medical image data by using the memory 210, the controller 220, and the communicator 270.

According to FIGS. 2A and 2B and the aforementioned descriptions, the controller 220 is presented as one block and controls overall operations of the data processing performed on the medical image data. However, the operations may not always be performed by the controller 220. Some of functions of the controller 220 may be performed by a functional unit that is presented as a separate block. For example, a function of generating hierarchy information regarding a hierarchy structure of an image group by analyzing respective pieces of original image data included in the image group may be performed by a hierarchy information generation unit, and a function of generating common data information based on the hierarchy information by extracting, from each piece of the original image data, common data elements regarding respectively classes that form the hierarchy structure may be performed by a common data information generation unit.

The operation of processing the original image data by the apparatus 200 for processing medical image data has been described. An operation of restoring the processed original image data will be described below. The operation of restoring the processed original image by the apparatus 200 for processing medical image data may be performed in an order opposite to the order of the operation of processing the original image data by the apparatus 200 for processing medical image data. Therefore, repeated descriptions will be omitted.

Figure 9A:
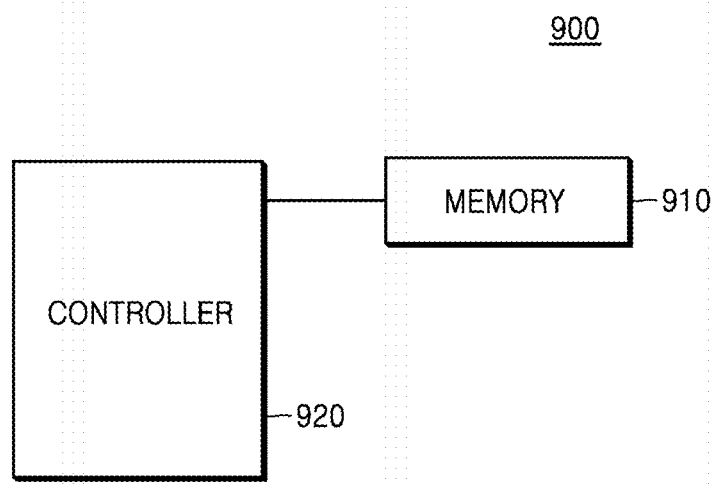
FIGS. 9A and 9B illustrate internal structures of apparatuses for processing medical image data according to another embodiment.
Figure 9B:
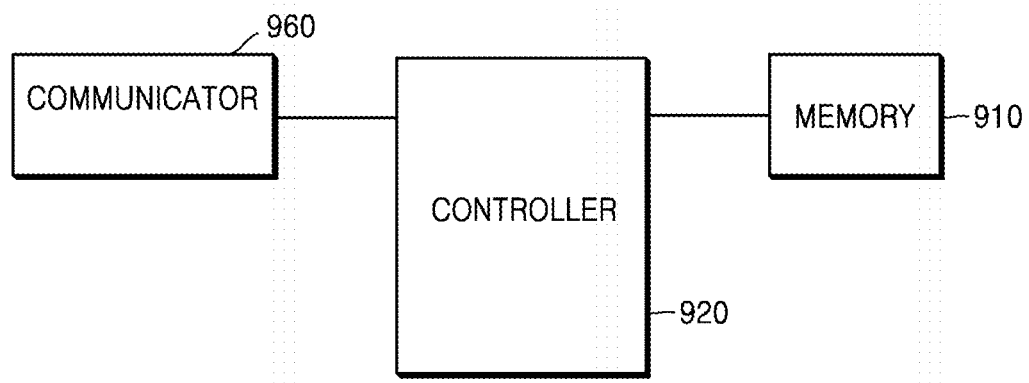

FIGS. 9A and 9B illustrate internal structures of apparatuses 900 and 950 for processing medical image data according to an embodiment.

Referring to FIG. 9A, the apparatus 900 for processing medical image data includes a memory 910 and a controller 920. The apparatus 900 for processing medical image data is included in the medical devices 110 and 140, the server 130, the portable device 150, and the like which are described with reference to FIG. 1 and may store the original image data. In more detail, the apparatus 900 for processing medical image data may restore compressed medical image data as the original image data. Furthermore, the compressed medical image data may be restored as the original image data by adding remaining data to common data elements in the medical image data.

The memory 910 according to an embodiment stores hierarchy information regarding a hierarchy structure of an image group generated based on the image group including pieces of original image data and common data information regarding common data elements regarding each class.

The controller 920 is a component for controller overall operations of the apparatus 900 for processing medical image data. In more detail, the controller 920 may control an operation of restoring the original image data with regard to the medical image data overall.

The controller 920 loads the common information including the hierarchy information and the common data information that are generated based on the pieces of the original image data, analyzes the hierarchy structure of the image group based on the hierarchy information included in the common information, analyzes the common data elements of each class that forms the hierarchy structure based on the common data information included in the common information, and restores at least one piece of the original image data based on analysis results. Operations of the controller 920 will be described below.

According to an embodiment, the controller 920 loads the common information including the common data information and the hierarchy information generated based on the pieces of the original image data. In this case, the common information may be information that is already generated and stored in the memory 910 or may be information received from another medical device and stored in the memory 910. Also, the common data information may include common meta information and common image binary information of each piece of the original image data.

According to an embodiment, the controller 920 analyzes the hierarchy structure of the image group based on the hierarchy information included in the common information and analyzes the common data elements of each class that forms the hierarchy structure based on the common data information included in the common information. In order to restore the original image data, the controller 920 analyzes which hierarchy structure is included in the image group and which pieces of common data are included in each hierarchy structure.

According to an embodiment, the controller 920 restores at least one piece of original image data based on an analysis result. The controller 920 does not repeatedly perform data processing on the common information that is duplicate data by restoring the original image data based on the common information and may perform the data processing at once. Therefore, image data processing efficiency may be improved.

According to an embodiment, when restoring at least one piece of the original image data based on the analysis result, the controller 920 may restore the at least one piece of the original image data by adding deleted common data elements to compressed image data from which the common data elements are deleted based on the common data information. In a general compression process, each piece of the original image data is restored such that compression efficiency may degrade. In an embodiment compared with the general compression process, the original image data is restored by adding the deleted common data elements to remaining data from which the common data elements are deleted such that compression efficiency may be improved. That is, compression and extraction are not repeatedly performed on the duplicate data, and thus the compression efficiency may be improved.

In this case, the controller 920 may add extracted common data elements regarding a third class to the compressed image data and may add extracted common data elements regarding a fourth class that is higher than the third class to the compressed image data. According to an embodiment, the third class may be an uppermost class. The common data elements are added in an order opposite to the order in which the data processing operation is performed, that is, an order from an upper class to a lower class.

The apparatus 900 for processing medical image data may further include a communicator (not shown). In this case, the controller 920 may receive/transmit data via the communicator.

Referring to FIG. 9B, the apparatus 950 for processing medical image data may further include a communicator 960 in comparison with the apparatus 900 for processing medical image data of FIG. 9A. Components that are included in both the apparatus 900 and the apparatus 950 for processing medical image data have the same respective reference numerals, and thus repeated descriptions thereof will be omitted.

The communicator 960 may receive/transmit data according to the control of the controller 920. In detail, the communicator 960 may communicate with an external device, an external medical device, or the like. For example, the communicator 960 may be connected to at least one of a medical device, a server, and a portable device which are connected to the outside. In detail, the communicator 960 is connected to an external medical imaging device and may receive the medical image data or may receive/transmit data necessary to process, compress and/or restore the medical image data. According to an embodiment, the communicator 960 may receive remaining data that remains after the common information and the common data elements are deleted from the pieces of the original image data included in the image group, according to the control of the controller 920.

According to an embodiment, when restoring the at least one piece of the original image data based on the analysis result, the controller 920 may restore the at least one piece of the original image data by adding the deleted common data elements to the remaining data based on the common data information. In this case, the controller 220 may identify the common data elements first based on the common information and then may add the common data elements to the remaining data while receiving each piece of the original image data. In a general transmission operation, respective pieces of image data are separately received and transmitted, and thus transmission efficiency may decrease. In an embodiment compared with the general transmission operation, common data elements are bound together as common information and received, and remaining data, which remains after the common data elements are bound together, are respectively received, thereby improving transmission efficiency. That is, duplicate data is transmitted and received once such that the transmission efficiency may be improved. Furthermore, other data processing is not performed on the original data, and the original data is separated from common data elements during a transmission operation. Thus, the image data may be immediately used in a medical device based on the current DICOM standard.

In this case, the controller 920 may extract common data elements regarding a third class, add the extracted common data elements to the remaining data, extract common data elements regarding a fourth class that is lower than the third class, and add the extracted common data elements to the remaining data. According to an embodiment, the third class may be an uppermost class. The original image data is restored by adding the common data elements to the remaining data in a direction in which the operation of processing the data is performed, that is, a direction from an upper class to a lower class.

Referring to FIGS. 9A and 9B and the aforementioned descriptions, the controller 920 is presented as one block and controls the operation of processing the medical image data overall. However, not every operation is performed by the controller 920. Some functions of the controller 920 may be performed by a functional unit that is presented as a separate block. For example, a function of analyzing the hierarchy structure of the image group based on the hierarchy information included in the common information may be performed by a hierarchy information analysis unit, and a function of analyzing common data elements regarding each class that forms the hierarchy structure based on the common data information included in the common information may be performed by a common data information analysis unit.

Also, the apparatus 900 for processing medical image data shown in FIGS. 9A and 9B may be the same as the apparatus 200 for processing medical image data shown in FIG. 2A. In this case, an apparatus for processing medical image data 900 may process and restore image data.

The operation of restoring the original image data by the apparatus 900 for processing medical image data has been described.

Overall operations of processing and restoring the original image data will be described below.

FIG. 10 illustrates an operation of compressing and restoring image data, according to an embodiment.

Referring to FIG. 10, the controller 920 generates compressed image data 1030 and common information 1040 by encoding original data 1010 in operation 1020. The controller 920 may generate the compressed image data 1030 by deleting common data elements from pieces of original image data 1010 included in an image group based on the generated common information 1040. In this case, as described above, the common information 1040 includes hierarchy information and common data information, and the common data information may include common meta information and common image binary information.

Also, the controller 920 restores original image data 1060 of a medical image 1002 by decoding, in operation 1050, the compressed image data 1030 and the common information 1040. The controller 920 may restore the original image data 1060 of a medical image by decoding the compressed image data 1030 and the common information 1040 in operation 1050.

In a general compression operation, respective pieces of original data are compressed and restored, and thus compression efficiency may decrease. In an embodiment compared with the general compression operation, the common data elements are managed as the common information 1040, the common data elements are deleted from the original image data 1010 for compression, and the original image data 1060 is restored by adding the deleted common data elements to remaining data other than the common data elements. Thus, compression efficiency may be improved. That is, duplicate pieces of data are not repeatedly compressed and decompressed, and thus the compression efficiency may be improved.

Figure 11:
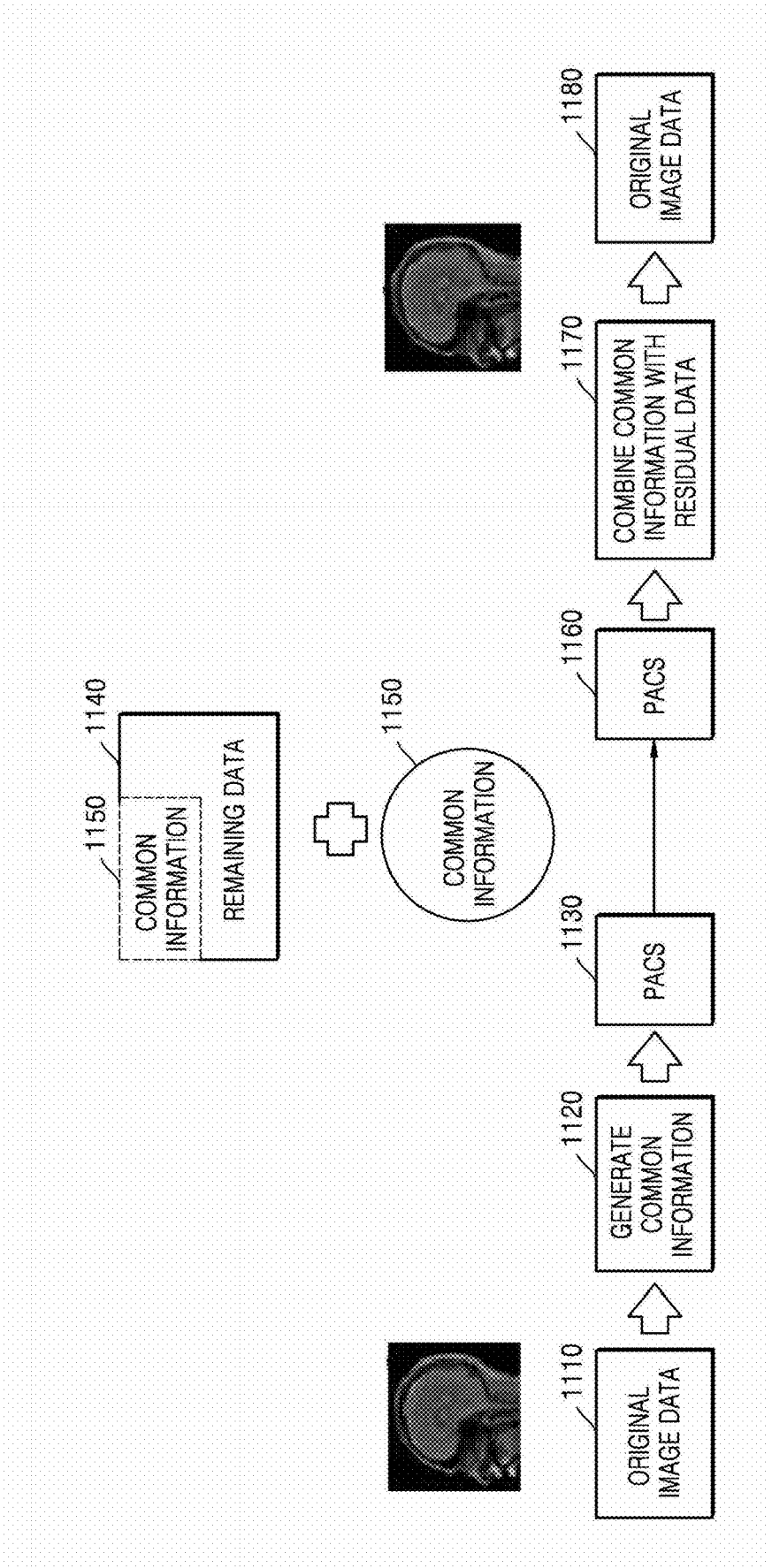
FIG. 11 illustrates ng an operation of transmitting and receiving image data according to an embodiment.

FIG. 11 illustrates an operation of transmitting and receiving image data, according to an embodiment.

Referring to FIG. 11, at an image data transmission side, the controller 920 generates common information with regard to original image data 1110 in operation 1120. The controller 920 transmits common information 1150 and remaining data 1140 other than the common information 1150 via a PACS 1130. In this case, as described above, the common information 1150 includes hierarchy information and common data information, and the common data information may include common meta information and common image binary information.

Also, at an image data reception side, the controller 920 receives the common information 1150 and the remaining data 1140 other than the common information 1150 via a PACS 1160. Then, the controller 920 combines the common information 1150 and the remaining data 1140 in operation 1170 and restores original image data 1180.

In a general data transmission operation, pieces of image data are individually transmitted, and thus transmission efficiency may decrease. In an embodiment compared with the general data transmission operation, the common elements are bound as common information for transmission, and remaining data other than the common data elements is transmitted, thereby improving transmission efficiency. That is, duplicate pieces of data are transmitted once, and thus the transmission efficiency may be improved. Furthermore, other data processing is not performed on original data, and the original data is separated from common data elements during a transmission operation. Thus, the image data may be immediately applied to a medical device according to the current DICOM standard.

Figure 12:
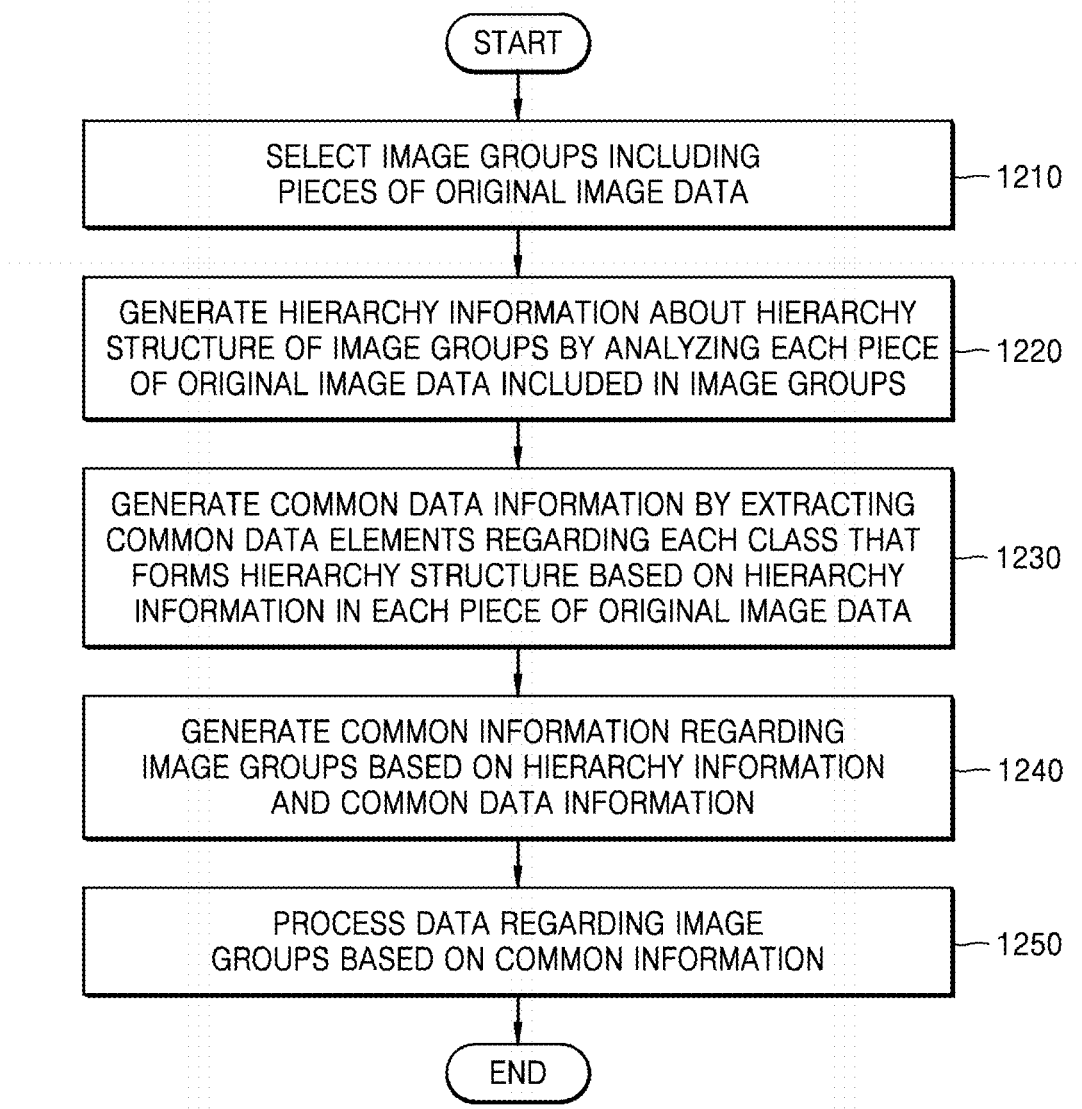
FIG. 12 illustrates a method of processing medical image data according to an embodiment.

FIG. 12 illustrates a method of processing medical image data according to an embodiment.

Referring to FIG. 12, in operation 1210, an image group including pieces of original image data is selected according to a DICOM standard.

Then, in operation 1220, hierarchy information regarding a hierarchy structure of the image group is generated by analyzing each piece of the original image data included in the image group. In this case, after pieces of image data are generated, the generated pieces of the image data may be selected as an image group according to a unit that is set. The set unit may be a time unit or a patient unit.

In operation 1230, common data elements regarding respective classes that form the hierarchy structure are extracted from each piece of the original image data based on the hierarchy information in order to generate common data information. In this case, common data elements regarding a first class are extracted, and common data elements regarding a second class that is higher than the first class are extracted from among the extracted common data elements regarding the first class. By deleting the common data elements regarding the second class from the common data elements regarding the first class, common data information may be generated. The first class may be a lowermost class. Also, the common data information may include common meta information and common image binary information of each piece of the original image data.

Then, in operation 1240, common information regarding the image group is generated based on the hierarchy information and the common data information.

Furthermore, in operation 1250, data processing is performed on the image group based on the common information. According to an embodiment, when the data processing is performed, the common data elements are deleted from each piece of the original image data included in the image group based on the common information, and thus compressed image data may be generated. Also, according to an embodiment, when the data processing is performed, the common information is transmitted to an external device, and remaining data that remains after the common data elements are excluded from the pieces of the original image data based on the common information may be transmitted to the external device.

Figure 13:
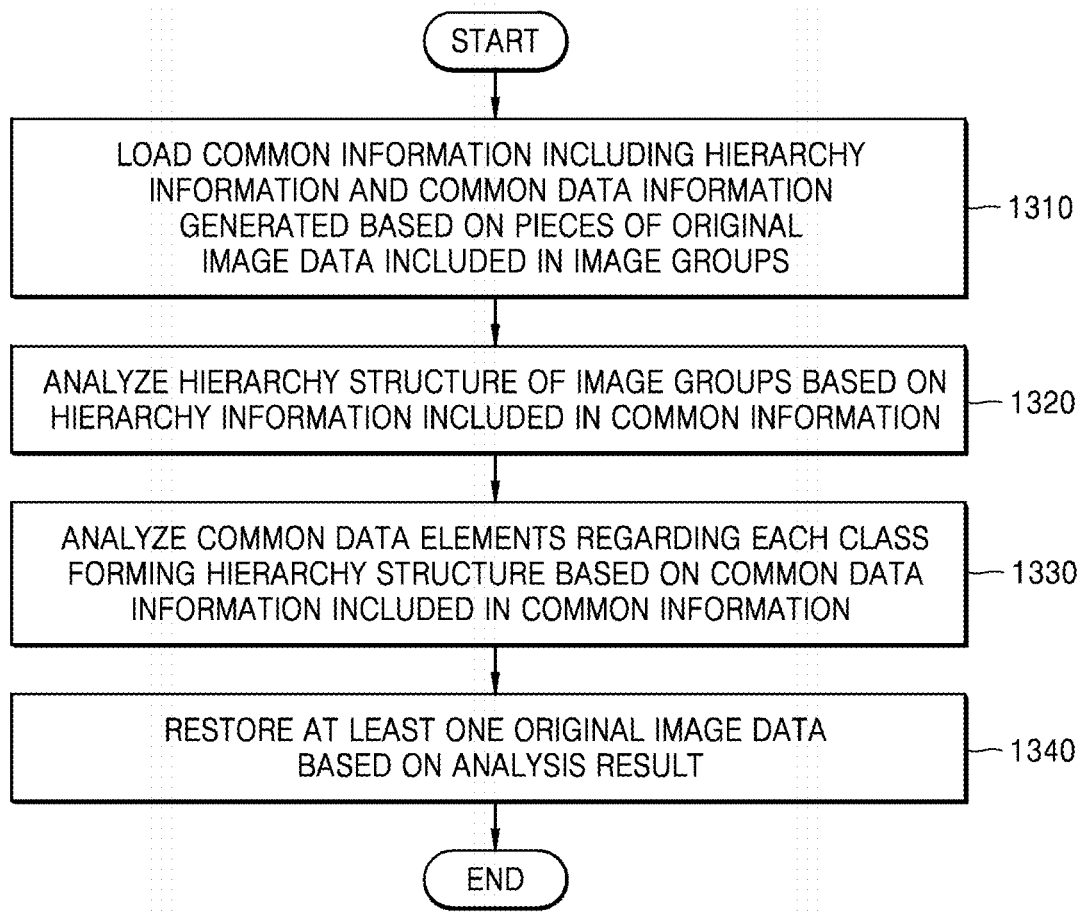
FIG. 13 illustrates a method of processing medical image data according to another embodiment.

FIG. 13 illustrates a method of processing medical image data according to another embodiment.

In operation 1310, common information including hierarchy information and common data information is loaded, the hierarchy information and the common data information being generated based on an image group including pieces of original image data according to a DICOM standard. According to an embodiment, before the common information is loaded, the common information may be received from an external device.

Then, in operation 1320, a hierarchy structure of the image group is analyzed based on the hierarchy information included in the common information.

In operation 1330, common elements regarding respective classes forming the hierarchy structure are analyzed based on the common information included in the common information. The common data information may include common meta information and common image binary information of each piece of the original image data.

In operation 1340, based on an analysis result, at least one piece of the original image data is restored. According to an embodiment, at least one piece of the original image data may be restored by adding, based on the common data information, deleted common data elements to compressed image data from which the common data elements are deleted. In this case, common data elements regarding a first class may be extracted and then added to the compressed image data, and common data elements regarding a second class that is lower than the first class may be extracted and then added to the compressed image data.

Also, according to an embodiment, the remaining data that remains after the common data elements are excluded from the pieces of the original image data included in the image group may be received. According to an embodiment, at least one piece of the original image data may be restored by adding the deleted common data elements to the remaining data based on the common data information. In this case, the common data elements regarding the first class may be extracted and then added to the compressed image data, and the common data elements regarding the second class that is lower than the first class may be extracted and then added to the compressed image data.

The embodiments described herein can be written as computer programs and can be implemented in general-use digital computers that execute the programs using a computer readable recording medium.

Examples of the computer readable recording medium include magnetic storage media (e.g., ROM, floppy disks, hard disks, etc.), optical recording media (e.g., CD-ROMs, or DVDs), etc.

It should be understood that embodiments described herein should be considered in a descriptive sense only and not for purposes of limitation. Descriptions of features or aspects within each embodiment should typically be considered as available for other similar features or aspects in other embodiments.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An apparatus for processing medical image data, the apparatus comprising:
a controller configured to:
select an image group comprising pieces of original image data using a digital imaging and communication in medicine (DICOM) standard;
generate hierarchy information regarding a hierarchy structure of the image group by analyzing each piece of the original image data comprised in the image group;
generate common data information by extracting, from each piece of the original image data, common data elements regarding respective classes that form the hierarchy structure based on the hierarchy information;
generate common information regarding the image group based on the hierarchy information and the common data information; and
perform data processing on the image group based on the common information; and
a memory configured to store the common information comprising the hierarchy information and the common data information,
wherein, when generating the common data information, the controller is further configured to:
extract common data elements regarding a first class;
extract common data elements regarding a second class from among the extracted common data elements regarding the first class, wherein the second class is higher than the first class; and
delete the common data elements regarding the second class from the common data elements regarding the first class.

2. The apparatus of claim 1, wherein the first class is a lowermost class.

3. The apparatus of claim 1, wherein, when the data processing is performed on the image group based on the common information, the controller is further configured to generate compressed image data by deleting the common data elements from each piece of the original image data comprised in the image group based on the common information.

4. The apparatus of claim 1, further comprising a communicator configured to receive/transmit data,
wherein, when the data processing is performed on the image group based on the common information, the controller is further configured to control the communicator to transmit the common information to an external device and transmit, to the external device, remaining data that remains after the common data elements are excluded from the pieces of the original image data comprised in the image group based on the common information.

5. The apparatus of claim 1, wherein, when the image group comprising the pieces of the original image data is selected, after pieces of image data are generated, the controller is further configured to select the generated pieces of the image data as the image group.

6. The apparatus of claim 5, wherein the controller selects the generated pieces of the image data as the image group based on time or patient.

7. The apparatus of claim 1, wherein the common data information comprises common meta information and common image binary information of each piece of the original image data.

8. An apparatus for processing medical image data, the apparatus comprising:
  a controller configured to:
    load common information comprising hierarchy information and common data information that are generated based on an image group comprising pieces of original image data using a digital imaging and communication in medicine (DICOM) standard;
    analyze a hierarchy structure of the image group based on the hierarchy information comprised in the common information;
    analyze common data elements regarding respective classes forming the hierarchy structure based on the common data information comprised in the common information; and
    restore at least one of the pieces of the original image data based on a result of both analyses; and
  a memory configured to store the common information comprising the hierarchy information and the common data information,
  wherein, when the at least one of the pieces of the original image data is restored based on the result of both analyses, the controller is further configured to:
    extract common data elements regarding a third class;
    add the extracted common data elements regarding the third class to compressed image data;
    extract common data elements regarding a fourth class that is lower than the third class; and
    add the extracted common data elements regarding the fourth class to the compressed image data.

9. The apparatus of claim 8, wherein, when the at least one of the pieces of the original image data is restored based on the result of both analyses, the controller, based on the common data information, is further configured to restore the at least one of the pieces of the original image data by adding deleted common data elements to the compressed image data from which the common data elements are deleted.

10. The apparatus of claim 9, wherein the third class is an uppermost class.

11. The apparatus of claim 8, further comprising a communicator configured to receive/transmit data,
  wherein the controller is further configured to control the communicator to receive remaining data that remains after the common information and the common data elements are excluded from the pieces of the original image data comprised in the image group, and
  when the at least one of the pieces of the original image data is restored based on the result of both analyses, the controller is further configured to restore the at least one of the pieces of the original image data by adding deleted common data elements to the remaining data based on the common data information.

12. The apparatus of claim 11, wherein, when the at least one of the pieces of the original image data is restored based on the result of both analyses, the controller is further configured to:
  extract common data elements regarding a third class;
  add the extracted common data elements regarding the third class to the remaining data, extract common data elements regarding a fourth class that is lower than the third class; and
  add the extracted common data elements regarding the fourth class to the remaining data.

13. The apparatus of claim 12, wherein the third class is an uppermost class.

14. The apparatus of claim 8, wherein the common data information comprises common meta information and common image binary information of each piece of the original image data.

15. A method of processing medical image data, the method comprising:
  selecting an image group comprising pieces of original image data using a Digital Imaging and Communication in Medicine (DICOM) standard;
  generating hierarchy information regarding a hierarchy structure of the image group by analyzing each piece of the original image data comprised in the image group;
  generating common data information by extracting common data elements regarding respective classes that form the hierarchy structure from each piece of the original image data, based on the hierarchy information;
  generating common information regarding the image group based on the hierarchy information and the common data information; and
  performing data processing on the image group based on the common information,
  wherein generating the common data information comprises:
    extracting common data elements regarding a first class;
    extracting common data elements regarding a second class that is higher than the first class from among the common data elements extracted from the first class; and
    deleting the common data elements regarding the second class from the common data elements of the first class.

16. The method of claim 15, wherein performing the data processing comprises generating compressed image data by deleting the common data elements from each piece of the original image data comprised in the image group based on the common information.

17. The method of claim 15, wherein selecting the image group comprising the pieces of the original image data comprises, after pieces of image data are generated, selecting the generated pieces of the image data as the image group.

* * * * *